US012797566B2

(12) United States Patent
Schwaibold

(10) Patent No.: US 12,797,566 B2
(45) Date of Patent: Nov. 17, 2026

(54) VENTILATOR WITH A SYNCHRONICITY INDEX

(71) Applicant: Loewenstein Medical Technology S.A., Luxembourg (LU)

(72) Inventor: Matthias Schwaibold, Karlsruhe (DE)

(73) Assignee: Loewenstein Medical Technology S.A., Luxembourg (LU)

(*) Notice: Subject to any disclaimer, the term of this patent is extended or adjusted under 35 U.S.C. 154(b) by 676 days.

(21) Appl. No.: 15/887,280

(22) Filed: Feb. 2, 2018

(65) Prior Publication Data

US 2018/0221608 A1 Aug. 9, 2018

(30) Foreign Application Priority Data

Feb. 3, 2017 (DE) ........................ 102017000980.5

(51) Int. Cl.

*A61M 16/00* (2006.01)
*A61M 16/06* (2006.01)
*A61M 16/08* (2006.01)

(52) U.S. Cl.

CPC ...... *A61M 16/024* (2017.08); *A61M 16/0003* (2014.02); *A61M 2016/0018* (2013.01); *A61M 2016/0021* (2013.01); *A61M 2016/0027* (2013.01); *A61M 2016/0036* (2013.01); *A61M 16/0066* (2013.01); *A61M 16/026* (2017.08); *A61M 16/06* (2013.01); *A61M 16/0683* (2013.01); *A61M 16/0858* (2014.02); *A61M 2205/18* (2013.01); *A61M 2205/3303* (2013.01); *A61M 2205/3331* (2013.01);

(Continued)

(58) Field of Classification Search

CPC .......... A61M 16/0003; A61M 16/0066; A61M 16/024; A61M 16/026; A61M 16/06; A61M 16/0683; A61M 16/0858; A61M 2016/0018; A61M 2016/0021; A61M 2016/0027; A61M 2016/0036; A61M 2205/18; A61M 2205/3303; A61M 2205/3331; A61M 2205/3334; A61M 2205/502; A61M 2205/52; A61M 2205/581; A61M 2205/583; A61M 2230/04; A61M 2230/10; A61M 2230/205; A61M 2230/40; A61M 2230/60; A61M 2230/63

USPC ............ 128/204.18, 204.12, 204.23, 204.21; 600/529

See application file for complete search history.

(56) References Cited

U.S. PATENT DOCUMENTS 9,027,552 B2 * 5/2015 Angelico .......... A61M 16/0003
128/204.23
9,586,018 B2 * 3/2017 Christopher ...... A61M 16/0666

(Continued)

*Primary Examiner* — Douglas Y Sul
(74) *Attorney, Agent, or Firm* — Abel Schillinger, LLP

(57) ABSTRACT

A ventilator comprising a ventilation device which produces a respiratory gas flow for ventilating at least one patient and sets the respiratory gas flow to at least one ventilation pressure depending on at least one respiratory phase of the patient. An monitoring device included in the ventilator is suitable and configured for monitoring a synchronicity between respiratory phase and target ventilation pressure by capturing a characteristic signal for the ventilation pressure and a characteristic signal for the respiratory phase of the patient and comparing the two signals to one another and determining a characteristic for the synchronicity on the basis of the comparison.

20 Claims, 4 Drawing Sheets

(52) U.S. Cl.
CPC ............... *A61M 2205/3334* (2013.01); *A61M 2205/502* (2013.01); *A61M 2205/52* (2013.01); *A61M 2205/581* (2013.01); *A61M 2205/583* (2013.01); *A61M 2230/04* (2013.01); *A61M 2230/10* (2013.01); *A61M 2230/205* (2013.01); *A61M 2230/40* (2013.01); *A61M 2230/60* (2013.01); *A61M 2230/63* (2013.01)

(56) References Cited

U.S. PATENT DOCUMENTS 10,064,583 B2 * 9/2018 Nakai ............... A61M 16/0051 128/204.23
10,137,266 B2 * 11/2018 Shelly ................. A61M 16/024
10,376,663 B2 * 8/2019 Sinderby ............ A61B 5/04884
2005/0027205 A1 * 2/2005 Tarassenko .......... A61B 5/0816 600/529
2005/0284476 A1 * 12/2005 Blanch .................. A61M 16/00 128/204.21
2009/0241955 A1 * 10/2009 Jafari ................ A61M 16/0666 128/204.23
2011/0029910 A1 * 2/2011 Thiessen ............. A61M 16/205 715/780
2012/0167885 A1 * 7/2012 Masic ............... A61M 16/0051 128/204.23
2015/0013674 A1 * 1/2015 Doyle .................. A61B 5/0816 128/202.22
2015/0090258 A1 * 4/2015 Milne ............... A61M 16/0051 128/204.23
2016/0166789 A1 * 6/2016 Enk ................... A61M 16/0816 128/204.25
2016/0193438 A1 * 7/2016 White ............... A61M 16/0069 128/204.23

* cited by examiner

VENTILATOR WITH A SYNCHRONICITY INDEX

CROSS-REFERENCE TO RELATED APPLICATIONS

The present application claims priority under 35 U.S.C. § 119 of German Patent Application No. 102017000980.5, filed Feb. 3, 2017, the entire disclosure of which is expressly incorporated by reference herein.

BACKGROUND OF THE INVENTION

1. Field of the Invention

The present invention relates to a ventilator having at least one ventilation device for producing a respiratory gas flow for ventilating at least one patient. The respiratory gas flow can be set to at least one ventilation pressure depending on at least one respiratory phase of the patient.

2. Discussion of Background Information

As a rule, ventilators identify a ventilation success by measuring tidal volume, tidal air, respiratory frequency and, sometimes, by measuring respiratory gases or blood gases as well.

If the ventilation success is unsatisfactory, a note regarding an unwanted system leak is usually output as a possible source of error in current ventilators.

However, a particularly decisive cause for restricted ventilation success can often also be found in a lack of synchronicity between pressure control and patient respiration. Here, as a rule, the ventilation pressure is not ideally adapted in time to the respective respiratory phase of the patient.

The lack of synchronicity may lead to the patient having to muster increased and, as a rule, very straining respiratory exertion in order to be able to follow the pressure control that has not been adapted in time. As a result, the ventilation success may be significantly impaired. However, identifying a lack of synchronicity is very time-consuming as a rule, and the staff require high levels of specialist knowledge. In a medical center, the lack of synchronicity may only be identified, as a rule, if it occurs at a time when there is monitoring by specialist staff. Moreover, special technical preconditions are also required, such as e.g. a very large screen for analyzing measurement signals and, in the case of an outsourced evaluation, a sufficiently fast data connection between the ventilator and workspace, too. The latter is a great disadvantage, particularly in the case of patients with home ventilation, since large amounts of data have to be transferred and evaluated in this case.

It is therefore desirable to significantly improve the identification of a lack of synchronicity during ventilation.

SUMMARY OF THE INVENTION

The present invention provides a ventilator which comprises at least one ventilation device which is suitable and configured for producing at least one respiratory gas flow for ventilating at least one patient and setting the respiratory gas flow to at least one ventilation pressure depending on at least one respiratory phase of the at least one patient. The at least one monitoring device is suitable and configured for monitoring a synchronicity between respiratory phase and target ventilation pressure and, to this end, capturing at least one characteristic signal for the ventilation pressure and at least one characteristic signal for the respiratory phase of the patient and comparing the two signals to one another and determining at least one characteristic for the synchronicity on the basis of the comparison.

In one aspect of the ventilator, the monitoring device may be suitable and configured for capturing and/or comparing at least one time curve of the characteristic signal for the ventilation pressure and/or at least one time curve of the characteristic signal for the respiratory phase, the monitoring device being suitable and configured for capturing a respiratory air flow or volume as a characteristic signal for the respiratory phase.

In another aspect, the monitoring device may be suitable and configured for comparing curves of the two signals to one another on the basis of at least one pattern recognition and identifying at least one characteristic functional feature in the curves of the signals.

In yet another aspect, the monitoring device may be suitable and configured for determining at least one similarity measure between the characteristic signal for the respiratory phase and the characteristic signal for the ventilation pressure on the basis of the comparison and, at least in part, using said similarity measure as a characteristic for the synchronicity.

In a still further aspect, the monitoring device may be suitable and configured for undertaking at least one preprocessing operation for at least one of the characteristic signals to be compared.

In another aspect, the ventilation device may be suitable and configured for predetermining at least one pressure profile depending on the respiratory phase of the at least one patient, the at least one pressure profile comprising a time-variable ventilation pressure.

In another aspect, the monitoring device may be suitable and configured for saving the characteristic for the synchronicity in at least one storage device and/or outputting said characteristic by at least one output unit and/or converting the characteristic into a control signal for a control device.

In another aspect, the monitoring device may be suitable and configured for saving and/or outputting at least one ventilation parameter in addition to the characteristic for the synchronicity.

In another aspect, the monitoring device may be suitable and designed for identifying at least one type of lack of synchronicity, in particular at least two types of lack of synchronicity, and using said at least one type of lack of synchronicity for determining the characteristic of the synchronicity, the at least one type of lack of synchronicity being taken from target ventilation pressures specified prematurely in relation to the respiratory phase of the at least one patient; target ventilation pressures specified belatedly in relation to the respiratory phase of the at least one patient; target ventilation pressures missed in relation to the respiratory phase of the at least one patient.

For example, the target ventilation pressures missed in relation to the respiratory phase of the at least one patient may comprise at least one missed target inspiration pressure and/or missed target expiration pressure and/or the target ventilation pressures specified prematurely in relation to the respiratory phase of the at least one patient may comprise a premature target inspiration pressure and/or premature target expiration pressure and/or the target ventilation pressures specified belatedly in relation to the respiratory phase of the at least one patient may comprise a belated target inspiration pressure and/or belated target expiration pressure.

Further, the monitoring device may be suitable and configured for identifying a missed target inspiration pressure by virtue of the characteristic signal for the respiratory phase at a defined time representing an exhalation phase and by virtue of the characteristic signal for the ventilation pressure indicating that the last target ventilation pressure set before the defined time is a target expiration pressure and not target inspiration pressure. For example, the monitoring device may be suitable and configured for identifying the characteristic signal representing the exhalation phase by virtue of a respiratory air flow of the at least one patient dropping below at least one threshold. The at least one threshold may define a respiratory air flow of less than or equal to 4 l/min for a period of time of more than half a second and of less than six seconds and/or the threshold may define a drop in the respiratory air flow of at least 5 l/min in relation to a maximum value of the respiratory air flow for a period of time of more than half a second and of less than six seconds.

Further, the monitoring device may be suitable and configured for identifying a belated target ventilation pressure by virtue of at least one characteristic functional feature in a time curve of the characteristic signal for the ventilation pressure occurring with a delay in relation to a corresponding characteristic functional feature in a time curve of the characteristic signal for the respiratory phase and by virtue of the delay reaching at least one threshold. For example, the threshold may be at least 100 ms and, preferably, at least 150 ms.

Even further, the monitoring device may be suitable and configured for counting a frequency of an occurrence of at least one of the types of lack of synchronicity during a defined time interval and at least partly taking these into account in the characteristic. For example, the monitoring device may be suitable and configured for capturing and counting target ventilation pressures that were set synchronously in relation to the respiratory phase of the at least one patient and at least relating the target ventilation pressures to the frequency of the occurrence of at least one of the types of lack of synchronicity and at least partly taking the ratio into account in the characteristic.

In another aspect of the ventilator, the monitoring device may be suitable and configured for identifying a premature target ventilation pressure by virtue of at least one characteristic functional feature in a time curve of the characteristic signal for the ventilation pressure occurring with a delay in relation to a corresponding characteristic functional feature in a time curve of the characteristic signal for the respiratory phase and by virtue of the delay dropping below at least one threshold. For example, the threshold may not more than 10 ms and, preferably, not more than 5 ms.

Further, the monitoring device may be suitable and configured for identifying ventilation refusal (fighting) of the at least one patient if the delay assumes a negative value such that the characteristic signal for the respiratory phase is delayed in relation to the characteristic signal for the ventilation pressure.

In another aspect of the ventilator, the monitoring device may be suitable and configured for identifying a missed and/or premature target ventilation pressure by virtue of at least one ventilation parameter derived from the characteristic signal for the ventilation pressure and/or the characteristic signal for the respiratory phase reaching or dropping below at least one threshold.

In another aspect, the monitoring device may be suitable and configured for identifying the occurrence of at least one type of lack of synchronicity by virtue of at least one similarity measure between the characteristic signal for the respiratory phase and the characteristic signal for the ventilation pressure reaching or dropping below at least one threshold.

In another aspect, the monitoring device may be suitable and configured for ascertaining a missed target ventilation pressure by virtue of at least one pattern recognition and, to this end, searching for at least one characteristic curve in a characteristic signal which does not occur in the other characteristic signal.

In another aspect, the monitoring device may be suitable and configured for ascertaining a belated and/or premature target ventilation pressure by way of pattern recognition and, to this end, searching for at least one time duration in time curves of the characteristic signals which leads to the greatest similarity of the characteristic signals in the case of a temporal displacement of at least one of the characteristic signals.

In another aspect, the monitoring device may be suitable and configured for ascertaining at least one deviation of at least one characteristic signal from at least one predicted value of the same signal, wherein a prediction function contains at least one earlier value of the same signal and a model equation.

In another aspect, the monitoring device may influence a function of the ventilation device, in particular of the control device, by way of information feedback about an occurrence of a lack of synchronicity, or type, frequency and strength thereof. For example, the feedback may influence the control device to change trigger sensitivities for spontaneous inspirations and expirations and/or a backup frequency and/or an inspiration duration for mandatory inspirations and expirations and/or an IPAP and/or an EPAP.

In another aspect of the ventilator, the characteristic for the synchronicity may be used, at least intermittently, for regulating or controlling or setting the target pressure.

The present invention also provides a method for operating at least one ventilation device of at least one ventilator, wherein at least one respiratory gas flow is produced for ventilating at least one patient and the at least one respiratory gas flow is set to at least one ventilation pressure depending on at least one respiratory phase of the patient. By at least one monitoring device, a synchronicity between respiratory phase and target ventilation pressure is monitored and, to this end, at least one characteristic signal for the ventilation pressure and at least one characteristic signal for the respiratory phase of the at least one patient are captured, the two characteristic signals are compared to one another, and at least one characteristic for the synchronicity is determined on the basis of the comparison.

As set forth above, the ventilator according to the invention comprises at least one ventilation device. The ventilation device is suitable and configured for producing at least one respiratory gas flow for ventilating at least one patient and setting the respiratory gas flow to at least one ventilation pressure depending on at least one respiratory phase of the patient. Here, the ventilator comprises at least one monitoring device. The monitoring device is suitable and configured for monitoring a synchronicity between respiratory phase and the target ventilation pressure and, to this end, capturing at least one characteristic signal for the ventilation pressure and at least one characteristic signal for the respiratory phase of the patient and comparing the two signals to one another. The monitoring device is suitable and configured for determining at least one characteristic for the synchronicity on the basis of the comparison.

The ventilator according to the invention offers many advantages. A particular advantage is offered by the monitoring device since this allows a significantly simpler and more economical control of the synchronicity. The characteristic created by the monitoring device, which, for example, may also be read and interpreted by patients or ancillary staff, is also particularly advantageous. Thus, specialist staff are not necessarily required to identify whether the target ventilation pressure is set synchronously with the respective respiratory phase of the patient. Faults or problems during the ventilation can be recognized and rectified quickly as a result of the improved monitoring of the synchronicity, such that the ventilation quality is significantly improved.

The ventilator, in particular the ventilation device and/or monitoring device, is preferably suitable and configured for also being able to carry out the features phrased as method steps within the scope of the present invention.

The term synchronicity within the scope of the present invention is understood to mean, in particular, a temporal correspondence. Here, the synchronicity may mean simultaneity. However, the synchronicity may also be a time offset. Merely by way of example, synchronicity is present if the target ventilation pressure follows or precedes the respiratory phase by a predetermined time interval, or if it is simultaneous therewith. Consequently, synchronicity is present, in particular, if a required temporal correspondence is maintained or if a limit is not exceeded or undershot. A lack of synchronicity is present, in particular, if the demanded temporal correspondence is not maintained.

The respiratory phase comprises, in particular, at least one exhalation phase and/or at least one inhalation phase, or it is embodied as such.

In particular, the ventilation device is suitable and configured for setting at least an inspiration pressure for an inhalation phase or inspiration of the patient and/or setting at least one expiration pressure for an exhalation phase or expiration. The inspiration pressure is embodied, in particular, as an IPAP (inspiratory positive airway pressure) and the expiration pressure is embodied, in particular, as an EPAP (expiratory positive airway pressure).

It is possible that at least one transition pressure may be set, in each case, between expiration pressure and inspiration pressure and/or between inspiration pressure and expiration pressure. The expiration pressure and/or inspiration pressure and/or transition pressure may be embodied as a pressure profile in each case. By way of example, the pressure profile may comprise at least one pressure ramp.

Preferably, the monitoring device is suitable and configured for capturing and/or comparing at least one time curve of the signal for the ventilation pressure and/or at least one time curve of the signal for the respiratory phase. A particularly reliable evaluation of the synchronicity is possible by using such signal curves. In particular, a time curve of the signal is the ventilation pressure as a function of time or the respiratory phase or the respiratory flow or the respiratory volume as a function of time. In particular, signals that are captured at the same time or signals that are captured with a time offset are compared to one another. For the comparison purposes, the signals may be normalized in time or brought into temporal correspondence.

In particular, the monitoring device is suitable and configured for capturing and/or comparing the signal for the ventilation pressure and/or the signal for the respiratory phase over a defined period of time. In particular, signals from the same periods of time are compared to one another. The periods of time for the comparison or for determining the characteristic comprise, in particular, at least one breath or preferably a plurality of breaths. The period of time may also comprise at least one minute and/or else at least one hour and/or at least one day. The period of time may also comprise at least one week or at least one month or else at least one year or more. Preferably, the period of time for the comparison or for determining the characteristic is adjustable by a user, for example by way of at least one operating device.

The monitoring device is preferably suitable and designed for capturing a respiratory air flow of the patient as a characteristic signal for the respiratory phase. The respiratory air flow offers very reproducible monitoring of the respiratory activity and consequently a reliable identification of the respiratory phases. The signal for the respiratory phase preferably corresponds to the respiratory air flow of the patient. The respiratory air flow signal describes, in particular, a volumetric flow per unit time in a flow connection between a blower device and a respiration interface of the patient. In particular, the signal for the respiratory air flow is compared to the signal for the ventilation pressure in order to ascertain the characteristic for the synchronicity. The respiratory air flow comprises, in particular, an exhalation flow and/or an inhalation flow.

The respiratory air flow may be captured, in particular, by at least one sensor device. Here, provision can be made of indirect or else direct capture. By way of example, the signal for the respiratory air flow may be captured by way of at least one flow sensor and/or pressure sensor. The signal for the respiratory air flow may also be captured on the basis of at least one operating state of at least one blower device. It is also possible to capture other suitable sensor means for capturing the respiratory air flow, e.g. the respiratory exertion (by means of an EMG sensor or esophagus pressure or otherwise) or the respiratory excursion (by means of belts with a measurement of the cross section or the ventilation movement or the measurement of jaw movements or others).

It is possible that the monitoring device is suitable and configured for comparing curves of the two signals to one another on the basis of at least one pattern recognition. Here, in particular, the monitoring device is suitable and configured for identifying at least one characteristic functional feature in the curves of the signals and searching for a pattern of the occurrence of the characteristic functional feature. Pattern recognition offers a particularly uncomplicated and, at the same time, reliable option for identifying a faulty synchronicity.

The monitoring device may be suitable and configured for determining at least one similarity measure between the signal for the respiratory phase and the signal for the ventilation pressure on the basis of the comparison and, at least in part, using said similarity measure as a characteristic for the synchronicity. A similarity measure is particularly meaningful for assessing the synchronicity.

In particular, the monitoring device is suitable and configured for undertaking at least one preprocessing operation for at least one of the signals to be compared. By way of example, a preprocessing operation may comprise smoothing of a time curve of the signal. The preprocessing operation may also comprise at least one removal of a mean value over a defined period of time, for example a signal that maps the leak or the purge flow in the case of the respiratory flow. The preprocessing operation may also comprise other suitable means for signal analysis or signal evaluation. By way of example, the preprocessing operation comprises at least one regression method and/or approximation method and/or at least one filter algorithm and/or at least one noise removal.

By way of such a preprocessing operation, the reproducibility of the ascertained characteristic may be significantly improved.

In an advantageous configuration, the ventilation device may be suitable and configured for setting at least one pressure profile depending on the respiratory phase of the patient. In particular, the pressure profile comprises at least one time-variable ventilation pressure. In particular, the pressure profile comprises at least two different ventilation pressures and preferably a multiplicity of different ventilation pressures. By way of example, the pressure profile defines the ventilation pressure as a function of time. However, it is also possible for the pressure profile to have a pressure curve that is constant over time. In particular, the inspiration pressure and/or the expiration pressure is set as a pressure profile. By way of example, at least one transition profile is provided between two pressure profiles.

The switchover between inspiration pressure and expiration or between corresponding pressure profiles is preferably effectuated in a manner triggered by a trigger which reacts to spontaneous respiratory exertions of the patient, or by way of a time control which triggers the mandatory inspirations or expirations.

In the case of triggering by the patient, there preferably is a reaction to pressure variations and/or variations of the respiratory flow and/or variations of the blower rotational speed. If a trigger is set to be very sensitive, i.e. with a high sensitivity, even small breaths are usually identified by the ventilation device. However, there may be additionally or prematurely triggered breaths, so called faulty triggers, in this case on account of variations in the signals, for example as a result of leaks or body movements or the pressure regulator of the ventilation device, leading to a lack of synchronicity. This may be subsequently identified by an evaluation of the signal curves, for example after triggering the trigger, by way of the monitoring device.

If the trigger is set to be insensitive, faulty triggering does not occur often but, instead, small breaths may be missed. If a time control is additionally active in this case, a backup frequency takes hold, with the latter triggering a mandatory breath. As a rule, the latter is not synchronous to the missed breath of the patient, but has a time delay. In an extreme case, the inspiratory pressure profile is already triggered by the time control when the patient has already started exhaling. This may also be subsequently identified by evaluating the signal curves by way of the monitoring device.

A time-controlled inspiration duration may additionally lead to a lack of synchronicity if the patient, for example, nevertheless exhales. In this case, the expiratory pressure profile is produced by the ventilation system with a time delay, in the extreme case only once the patient has already started inhaling again.

A time control may also lead to inspiration pressures and expiration pressures being predetermined prematurely if the inspiration times or breathing times for the patient are set to be too short. These cases may also be subsequently identified by evaluating the signal curves by way of the monitoring device.

It is particularly preferred in all configurations that the monitoring device is suitable and configured for saving the characteristic for the synchronicity in at least one storage device and/or outputting said characteristic by means of at least one output unit. This is advantageous in that a faulty synchronicity can be identified independently in time of the occurrence thereof. As a result, it is no longer necessary for appropriately educated specialist staff to be present precisely when the pressure targets do not follow the respiratory phase of the patient. Moreover, the characteristic saved in the storage device may also be read and evaluated with spatial separation from the ventilator.

The storage device and the output device preferably have a functional interconnection. The storage device may comprise a securely installed storage medium and/or at least one replaceable storage medium, for example at least one memory card. It is possible for the characteristic to be stored locally in the ventilator and/or outside of the ventilator in at least one network and/or one database.

The output unit comprises e.g. at least one screen and/or at least one display. The output unit may also comprise at least one loudspeaker, by means of which the characteristic may be effectuated in the form of a warning notification and/or as a speech output. Displaying the characteristic moreover offers the advantage of allowing the synchronicity to be assessed quickly and with little outlay and, for example, by simply looking at the output unit. As a result, the complicated analysis of complex signal curves on large screens or long printouts is no longer necessary.

It is possible for the output unit and/or the storage device to be housed in the ventilator. However, it is also possible for the output unit and/or the storage device to be embodied separately and be situated outside of the ventilator. Then, the ventilator is connectable, at least intermittently, to the output unit and/or the storage device, in particular by way of at least one network connection or data connection. Provision can be made of a wired and/or wireless or radio-based connection.

The monitoring device may be suitable and configured for saving and/or outputting at least one ventilation parameter in addition to the characteristic for the synchronicity. To this end, the monitoring device has a functional connection with, in particular, at least one sensor means for capturing at least one ventilation parameter. In particular, at least one measure for a ventilation success may be ascertained on the basis of the ventilation parameter. By way of example, the ventilation parameter is characteristic for a leak and/or for a volume and/or for a respiratory frequency and/or for an apnea-hypopnea index. Thus, there may also be an assessment of further ventilation parameters together with the assessment of the synchronicity on the basis of the characteristic.

It is particularly preferred in all configurations that the monitoring device is suitable and designed for identifying at least one type of lack of synchronicity and preferably at least two types of lack of synchronicity and using said at least one type of lack of synchronicity for determining the characteristic of the synchronicity. In particular, the at least one type of lack of synchronicity is taken from at least one group of types of lack of synchronicity, comprising: target ventilation pressures specified prematurely in relation to the respiratory phase of the patient; target ventilation pressures specified belatedly in relation to the respiratory phase of the patient; target ventilation pressures missed in relation to the respiratory phase of the patient. These types of lack of synchronicity are of particularly decisive importance for the ventilation quality. In particular, a missed target ventilation pressure is understood to mean a target that was not even set or inadvertently omitted.

The target ventilation pressures missed in relation to the respiratory phase of the patient comprise, in particular, at least one missed target inspiration pressure and/or missed target expiration pressure. The target ventilation pressures specified prematurely in relation to the respiratory phase of the patient comprise, in particular, at least one premature target inspiration pressure and/or premature target expiration pressure. The target ventilation pressures specified belatedly in relation to the respiratory phase of the patient comprise, in particular, at least one belated target inspiration pressure and/or belated target expiration pressure.

Preferably, the monitoring device is suitable and designed for identifying a missed target inspiration pressure by virtue of the signal for the respiratory phase at a defined time representing an exhalation phase and by virtue of the signal for the ventilation pressure indicating that the last target ventilation pressure set before the defined time is a target expiration pressure and not target inspiration pressure. However, it is also possible for the last target ventilation pressure set before the defined time to be a target transition pressure which is set after an expiration pressure and before an inspiration pressure. Here, a time may also be embodied as a period of time.

By way of example, a missed target inspiration pressure is identified by virtue of the signal for the respiratory phase representing an exhalation phase and the target pressure being in a waiting phase for a missed inhalation phase.

Here, the monitoring device is preferably suitable and designed for identifying the signal representing the exhalation phase by virtue of a respiratory air flow dropping below at least one threshold. However, identification is also possible by virtue of the respiratory air flow as a function of time having a characteristic functional feature, for example a slope, and by virtue of the functional feature exceeding or dropping below a threshold.

In particular, the threshold defines a respiratory air flow of less than or equal to about 4 l/min for a period of time of more than half a second and of less than six seconds. It is also possible for the threshold to define a drop in the respiratory air flow of at least about 5 l/min in relation to a maximum value of the respiratory air flow for a period of time of more than half a second and of less than six seconds. In particular, the maximum value of the respiratory air flow corresponds to the highest value of the respiratory air flow which was captured since the last identified exhalation phase and/or the last set target expiration pressure and/or in a waiting phase for an inhalation phase. Other suitable thresholds are also possible, for example the drop in the respiratory air flow in relation to a maximum value by a percentage which preferably changes over time; preferably, the percentage lies between about 10% and about 90%.

In particular, the monitoring device is suitable and designed for identifying a missed target inspiration pressure by virtue of the signal for the respiratory phase at a defined time representing an inhalation phase and the signal for the ventilation pressure indicating that the last set target ventilation pressure before the defined time being a target inspiration pressure and not a target expiration pressure. Ascertaining the signal representing the inhalation phase is effectuated, in particular, in a manner analogous to the above-described steps for identifying a missed target inspiration pressure. In particular, the missed target inspiration pressure is identified by virtue of the respiratory air flow exceeding or dropping below at least one threshold.

Preferably, the monitoring device is suitable and designed for identifying a belated target ventilation pressure by virtue of at least one characteristic functional feature in a time curve of the signal for the ventilation pressure occurring with a delay in relation to a corresponding characteristic functional feature in a time curve of the signal for the respiratory phase and by virtue of the delay reaching at least one threshold. The characteristic functional feature is, for example, a minimum and/or a maximum, a point of inflection, a saddle point, an asymptote and/or a different suitable feature of a function. The characteristic functional feature may also be a gradient and preferably a maximum and/or minimum and/or average gradient. A particularly uncomplicated and robust implementation is provided by comparison of the time curves of respiratory air flow and ventilation pressure at the start of the inspiration, wherein the time difference between the time of reaching a percentage of the maximum respiratory air flow, for example about 40% or about 50% or about 60%, and the time of reaching a percentage of the inspiratory pressure difference (IPAP–EPAP), for example about 40% or about 50% or about 60%, is measured.

In particular, the monitoring device is suitable and designed for identifying the characteristic functional feature on the basis of the computational operation that is conventional for functional analysis. The computational operations are saved in the monitoring device.

The threshold for identifying a belated target ventilation pressure is, in particular, at least about 100 ms and, preferably, at least about 150 ms, Such a threshold is particularly suitable since, in the normal case, the pressure control follows the respiratory phase with a time difference of between 0 ms and about 100 ms.

The monitoring device is preferably suitable and designed for identifying a premature target ventilation pressure by virtue of at least one characteristic functional feature in a time curve of the signal for the ventilation pressure occurring with a delay in relation to a corresponding characteristic functional feature in a time curve of the signal for the respiratory phase and by virtue of the delay dropping below at least one threshold.

In particular, the threshold is about 10 ms or less, and preferably about 5 ms or less. It is also possible for the threshold to be about 2 ms or less. The threshold may also be zero. It is also possible for the threshold to have a negative sign.

In an advantageous configuration, the monitoring device is suitable and designed for identifying ventilation refusal (fighting) of the patient if the delay assumes a negative value such that the signal for the respiratory phase is delayed in relation to the signal for the ventilation pressure. Identifying a premature target ventilation pressure which leads to a ventilation refusal of the patient is a particular advantage of the ventilator according to the invention and significantly improves the ventilation quality. The monitoring device may be suitable and designed for identifying ventilation refusal by the patient if the signal for the respiratory phase indicates a respiratory air flow below a threshold. In particular, the threshold is less than zero or a negative value.

It is also possible for the monitoring device to be suitable and configured for identifying a missed and/or premature target ventilation pressure by virtue of at least one ventilation parameter derived from the signal for the ventilation pressure and/or the signal for the respiratory phase reaching or dropping below at least one threshold. The threshold in this case describes, in particular, a temporal rate of change and, for example, a gradient of the signal as a function of time. As a rule, such ventilation parameters have corresponding changes in the case of a missed or premature target ventilation pressure, and so these may also be used very reliably for the purposes of identifying the lack of synchronicity. The derived ventilation parameter is, in particular, a respiratory frequency and/or a respiratory volume and/or an inspiration time or expiration time and/or the ratio of the two or of one of the two and the breath duration.

By way of example, a derived ventilation parameter with a temporal rate of change above or below a threshold is provided for identifying a premature and/or missed target ventilation pressure. By way of example, a missed target ventilation pressure may be identified by virtue of the respiratory frequency dropping to about 70% or less of the spontaneous respiratory frequency. A premature target ventilation pressure may be identified by virtue of, for example, the respiratory frequency increasing to about 130% or more of the spontaneous respiratory frequency.

The Applicant reserves the right to claim a ventilator which comprises at least one monitoring device which is suitable and configured for monitoring the synchronicity of ventilation pressure and respiratory phase, and identifying a missed and/or premature target ventilation pressure in relation to the respiratory phase of the patient by virtue of at least one ventilation parameter that is derived from a signal for the ventilation pressure and/or a signal for the respiratory phase reaching or dropping below at least one threshold. Such a ventilator facilitates a very reliable and, at the same time, uncomplicated identification of a missed or premature target ventilation pressure.

It is also possible for the monitoring device to be suitable and configured for identifying the occurrence of at least one of the types of lack of synchronicity by virtue of one similarity measure between the signal for the respiratory phase and/or respiratory air flow and/or respiratory volume and the signal for the ventilation pressure reaching and/or dropping below at least one threshold. Since the similarity measure increases or falls in a characteristic manner in the case of a lack of synchronicity, such a configuration offers a particularly reliable identification of a faulty synchronicity. A similarity measure may be embodied as a correlation coefficient of the signals to be compared or as a regression.

The monitoring device may also be suitable and configured for ascertaining a missed target ventilation pressure by at least one pattern recognition. In particular, the monitoring device is suitable and configured for identifying at least one characteristic curve in a signal for the pattern recognition which does not occur in another signal. By way of example, such a characteristic curve is a missing deflection or a missing maximum and/or minimum in the signal of the ventilation pressure. Such pattern recognition can be implemented in a technically uncomplicated way and, at the same time, offers a reliable identification of missed target ventilation pressures.

The monitoring device may also be suitable and configured for ascertaining a belated and/or premature target ventilation pressure by at least one pattern recognition and, to this end, searching for at least one time duration in the time curve of the signals which, in the case of a temporal displacement of at least one of the signals, leads to the greatest similarity of the signals, for example by way of searching for the highest correlation coefficient. Here, provision can be made for the time duration having to exceed at least one threshold so that a lack of synchronicity is identified. Thus, a belated or premature target ventilation pressure can be identified very reliably.

What is particularly preferred in all configurations is that the monitoring device is suitable and configured for counting the frequency or strength of the occurrence of at least one of the types of lack of synchronicity during a defined time interval and taking this into account for the characteristic. Such a characteristic offers a very informative statement about the synchronicity and is therefore particularly helpful when assessing the ventilation success.

The characteristic may describe the frequency of the occurrence of at least one of the types of lack of synchronicity during a defined time interval. By way of example, the characteristic may comprise at least one separate counter in each case for the missed and/or belated and/or premature target ventilation pressure. However, it is also possible for the characteristic to comprise a common counter for two or more types of lack of synchronicity. Here, provision can be made of a weighting (prioritization) for one or more types of lack of synchronicity. By way of example, the counter for missed targets may be incorporated more strongly in the characteristic than a belated or premature target ventilation pressure. Here, the counter may be embodied in such a way that, for example, it counts time units, e.g. seconds, or events, e.g. breaths.

By way of example, the time interval within which the occurrence of the lack of synchronicity is counted may be at least one minute. An interval of at least two minutes or of at least about five minutes or of at least about seven minutes or else of at least about 15 minutes is also possible. The interval may also be at least about 20 minutes or at least about 30 minutes or else one or more hours. An interval of one or two or more days is also possible. The interval may also be one or more weeks or else one month or more. An interval of one or more years is also possible. The interval may also be adjustable by way of an operating device.

Preferably, the monitoring device is suitable and configured for capturing and counting a target ventilation pressure that was set synchronously in relation to the respiratory phase of the patient. Here, the monitoring device is particularly preferably suitable and configured for at least relating the frequency of the synchronously set targets to the frequency of the occurrence of at least one of the types of lack of synchronicity and at least partly taking into account the ratio in the characteristic. As a result of such a characteristic, the ventilation quality may be represented very clearly and, at the same time, in a particularly meaningful way. In particular, the characteristic describes a ratio of the lack of synchronicity to synchronously set target ventilation pressures, or vice versa Here, the ratio for individual types of lack of synchronicity may be ascertained separately. It is also possible for the ratio for two or more types of lack of synchronicity to be ascertained together and processed to form a characteristic. Here, it is possible to provide a weighting for certain types of lack of synchronicity.

It is possible for the monitoring device to comprise at least one detector unit. In particular, the detector unit is suitable and configured for identifying at least one type of lack of synchronicity and/or one synchronously set target ventilation pressure. At least one detector unit may be respectively provided for each type of lack of synchronicity. It is also possible for one common detector unit to be provided for identifying two or more types of lack of synchronicity. In particular, the detector unit counts a frequency of the occurrence of the respective type of lack of synchronicity.

It is possible for the monitoring device to comprise at least one integration unit. In particular, the integration unit is suitable and designed for combining the frequency of the individual types of lack of synchronicity and/or synchronously set target ventilations by calculation and ascertaining at least one overall measure for the frequency of the lack of synchronization.

The method according to the invention serves to operate at least one ventilation device of at least one ventilator. At least one respiratory gas flow for ventilating at least one patient is produced. The respiratory gas flow is set to at least one ventilation pressure depending on at least one respiratory phase of the patient. Here, a synchronicity between the respiratory phase of the patient and the target ventilation pressure is monitored by means of at least one monitoring device. To this end, at least one characteristic signal for the ventilation pressure and at least one characteristic signal for the respiratory phase of the patient are captured. The two signals are compared to one another. At least one characteristic for the synchronicity is determined on the basis of the comparison.

The method according to the invention also offers many advantages and facilitates particularly uncomplicated and reliable monitoring of the synchronicity.

The monitoring device may comprise at least one sensor device for capturing the signal for the ventilation pressure and/or the signal for the respiratory phase. The monitoring device may also have a functional connection to a sensor device of the ventilation device such that the signal for the ventilation pressure and/or the signal for the respiratory phase may be obtained from the ventilation device.

In particular, at least one algorithm for signal processing and/or for determining the characteristic is saved in the monitoring device. In particular, the thresholds and/or limit values are also saved in the monitoring device.

The ventilation pressure can preferably be captured by at least one sensor device. A direct capture or else an indirect capture is possible. By way of example, the ventilation pressure may be captured by way of at least one pressure sensor and/or flow sensor and/or any other suitable sensor means. It is also possible for the ventilation pressure to be able to be captured on the basis of at least one operating state of at least one blower device.

In particular, the ventilation device comprises at least one control device for setting the ventilation pressure or for predetermining the ventilation pressure.

By way of example, the monitoring device is able by way of feedback of the information about the occurrence of a lack of synchronicity or the type, frequency and strength thereof to influence the ventilation device, in particular the control device. The feedback preferably acts on the trigger sensitivities for spontaneous inspirations and expirations and/or on the backup frequency and inspiration duration for mandatory inspirations and expirations.

By way of example, if there is a missed or delayed target IPAP, the sensitivity of the inspiration trigger is increased, for example by lowering the trigger threshold, or the backup frequency, by means of which mandatory breaths are triggered by the ventilator, is increased.

By way of example, if there is a missed or delayed target EPAP, the sensitivity of the expiration trigger is increased, for example by lifting the trigger threshold, or the inspiration duration, after which a mandatory exhalation is triggered, is reduced.

By way of example, if there is a premature target IPAP, the sensitivity of the inspiration trigger is lowered, for example by lifting the trigger threshold, or the backup frequency, with which mandatory breaths are triggered by the ventilator, is reduced.

By way of example, if there is a premature target EPAP, the sensitivity of the expiration trigger is reduced, for example by lowering the trigger threshold, or the inspiration duration, after which a mandatory exhalation is triggered, is increased.

Alternatively, or in a complementary manner, the invention relates to a ventilator having at least one ventilation device, which is suitable and configured for producing at least one respiratory gas flow for ventilating a patient and setting the respiratory gas flow to at least one ventilation pressure depending on at least one respiratory phase of the patient, characterized by at least one monitoring device which is suitable and configured for monitoring a synchronicity between respiratory phase and target ventilation pressure (IPAP or EPAP) and, to this end, capturing at least one characteristic signal for the ventilation pressure and at least one characteristic signal for the respiratory phase of the patient and comparing the two signals to one another and determining at least one characteristic for the synchronicity on the basis of the comparison, wherein the control device e.g. implements the target ventilation parameters or ventilation parameter settings such as pressure, flow, times, frequencies depending on the extent of the synchronicity.

Alternatively, or in a complementary manner, the invention relates to a ventilator having at least one ventilation device, which is suitable and designed for producing at least one respiratory gas flow for ventilating a patient and setting the respiratory gas flow to at least one ventilation pressure depending on at least one respiratory phase of the patient, characterized by at least one monitoring device which is suitable and configured for monitoring a synchronicity between respiratory phase and target ventilation pressure (IPAP or EPAP) and, to this end, capturing at least one characteristic signal for the ventilation pressure and at least one characteristic signal for the respiratory phase of the patient and comparing the two signals to one another and determining at least one characteristic for the synchronicity on the basis of the comparison, wherein the characteristic for the synchronicity is used, at least intermittently, for regulating or controlling or setting the target pressure.

BRIEF DESCRIPTION OF THE DRAWINGS

Further advantages and features of the present invention emerge from the description of the exemplary embodiments, which are explained below with reference to the attached figures.

In the figures.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
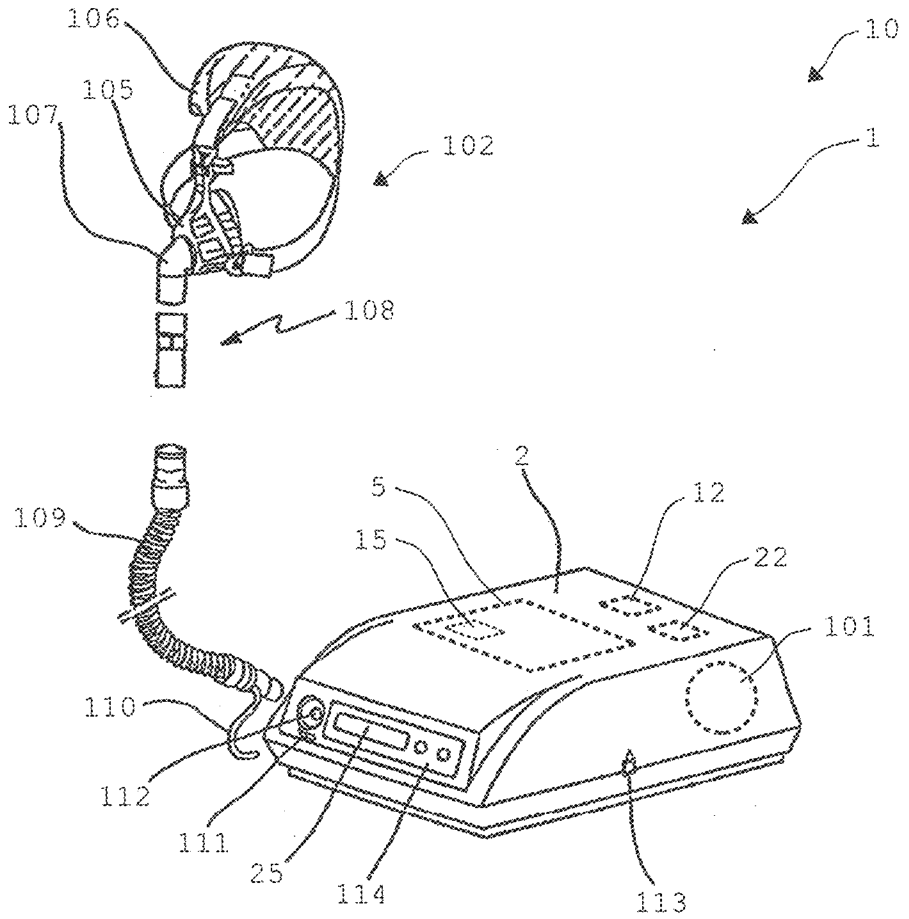
FIG. 1 shows a purely schematic illustration of a ventilator according to the invention.

FIG. 1 shows a ventilator 1 (or 10) according to the invention, which is embodied here as a home ventilator or as a sleep therapy appliance. However, the ventilator 1 may also be embodied as a clinical ventilator 1. The ventilator 1 is suitable and designed for carrying out the method according to the invention.

Operating and adjusting the ventilator 1 is effectuated by way of a user interface 114 having operating elements 103 and an output unit 25. By way of example, the output unit 25 may comprise a display with or without a touch-sensitive surface.

The ventilator 1 comprises a ventilation device 2 having a blower device 101 for producing a respiratory gas flow or an air flow for the ventilation. A defined ventilation pressure is applied to the respiratory gas flow. The ventilation pressure is adjustable, and so a different pressure is provided to the patient, e.g. in an inhalation phase, than in an exhalation phase or an intermediate phase.

The ventilator 1 has a respiration interface 102 in order to supply the air flow to a user for ventilation purposes. The respiration interface 2 shown here is a ventilation mask 105 embodied as a nasal mask. A head gear 106 is provided for anchoring the ventilation mask 105. The respiration interface 102 may also be configured, for example, as a full-face mask, as a nasal pillow, as a tube or as a laryngeal mask.

For the purposes of connecting the respiration interface 102 to the ventilation device 2, provision is made of a connection tube 109 which is connected to the ventilation device 2 by means of a coupling device 112. The connection tube 109 is connected to the respiration interface 102 by means of a coupling element 107. Here, an exhalation element 108 is arranged between the connection tube 109 and the coupling element 107, said exhalation element comprising a valve or being embodied as the latter. In particular, the exhalation element 108 is provided to prevent a return breath into the ventilator 1 while the user exhales. Here, the ventilation device 2 is functionally connected to a sensor device 22 which has one or more sensor means for capturing appliance parameters and/or patient parameters and/or other variables that are characteristic for the ventilation.

By way of example, the sensor device 22 comprises a pressure sensor (not shown in any more detail here) which captures the pressure conditions in respect of the respiration interface 102. To this end, the pressure sensor is connected to the respiration interface 102 by way of a pressure measuring tube 110. The pressure measuring tube 110 is connected to the monitoring device 21 by way of an input nozzle 111.

Here, the ventilation device 2 comprises a control device 12 for actuating the blower device 101. The control device 12 may provide a necessary minimum pressure and/or compensate pressure variations caused by the respiratory activity of the user. By way of example, the control device 12 captures the current pressure in the ventilation mask 105 by means of the sensor device 22 and accordingly updates the power of the blower device 101 until a desired ventilation pressure is present.

The apparatus parameters required to adjust the ventilation device 2 and the appliance configurations and/or appliance software are saved in a storage device 15.

Here, the sensor device 22 may also be embodied to capture patient parameters. To this end, it is equipped with sensor means for measuring the respiration excursion, for measuring a blood oxygen saturation and/or for measuring an EEG, EMG, FOG or ECG activity.

The ventilator 1 shown here offers an adjustment of the ventilation pressure or a pressure control which assists the breathing of the patient with at least two pressure levels.

Figure 4:
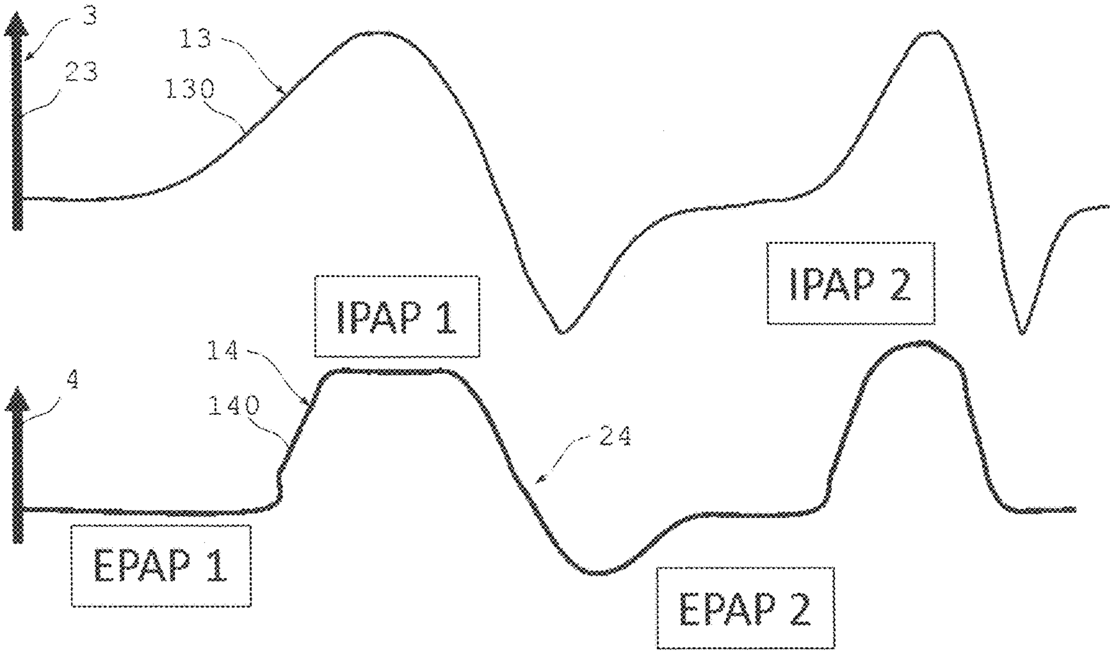
FIG. 4 shows a purely schematic diagram for sketching out a synchronicity between respiratory phase and ventilation pressure.

For the purposes of elucidating such a pressure control, FIG. 4 shows, in the lower diagram, a sketched out curve 140 of a signal 14 of the ventilation pressure 4 over time. The upper diagram sketches the corresponding curve 130 of a signal 13 of the respiratory air flow 23 of the patient over time. It is possible to identify characteristic changes in the curve which are caused by the changing respiratory phases 3 of the patient.

The apparatus outputs a first pressure profile (inspiratory positive airway pressure, IPAP) in at least part of the inspiratory phase of the patient; the apparatus outputs a second pressure profile (expiratory positive airway pressure, EPAP) in at least part of the expiratory phase of the patient. As a rule, the IPAP profile has an elevated pressure curve in relation to the EPAP profile. As a result, the lungs of the patient are at least partly mechanically ventilated; the respiratory muscles of the patient are relieved or said patient's respiratory volume is increased or at least stabilized.

The IPAP profile may have a constant pressure curve or a variable curve 140. By way of example, the variable curve 140 may be embodied as a pressure profile 24. As a result of this, it is possible to follow the respiratory contour of the patient in an improved manner.

The EPAP profile may also have a constant pressure curve or a variable curve 140 or a pressure profile 24. Here, the ventilation device 2 applies a transition profile, e.g. in the form of pressure ramps, between the IPAP profile and EPAP profile.

The transition between IPAP and EPAP may be triggered by a trigger when the ventilation device 2 identifies the start or end of a respiratory phase 3 or respiratory exertion of the patient. The transition may also be triggered under time or volume control, for example if no beginning or no end of a respiratory phase 3 or of respiratory exertion can be identified after the expiry of a waiting time.

The ventilator 1 according to the invention is equipped with a monitoring device 5 for monitoring the synchronicity or the desired temporal correspondence of target pressure and respiratory phase 3.

Such a monitoring device 5 is particularly advantageous since a lack of synchronicity between pressure control and patient respiration is a frequent cause for restricted ventilation success. By way of example, a lack of synchronicity means that the IPAP profile of the appliance 1 is not produced at the time of maximum inhalation by the patient or that the EPAP profile is not produced at the time of maximum exhalation by the patient. A lack of synchronicity may also mean that the patient follows the appliance 1 with their respiration contour because said apparatus prematurely triggers the transition phases between IPAP and EPAP without an actual respiratory exertion of the patient being present and without a predetermined waiting time having expired.

By way of example, the synchronicity is impaired if individual small breaths of the patient are not identified by the appliance 1. Thereupon, the appliance 1 repeatedly identifies the expiry of the predetermined waiting time and, for example, produces mandatory transitions between EPAP profile and IPAP profile, even though the patient is currently in the exhalation phase of their breath that was missed by the appliance 1. As a result, the ventilation success can be significantly impaired.

Here, the monitoring device 5 identifies at least two types of lack of synchronicity between respiratory phase 3 or respiratory air flow 23 of the patient and pressure control by the ventilation device 2 for a predefined evaluation time period. The monitoring device 5 ascertains at least one characteristic 6 or a measure of the synchronicity for this evaluation time period.

The evaluation time period may be one breath or one respiratory phase. The evaluation time period may also be one to a number of minutes or else one to a number of days. In a preferred embodiment, the evaluation time period is adjustable by at least one user.

The characteristic 6 is stored by the monitoring device 5 and for example saved in the storage device 15. The data may also be saved on a replaceable storage medium 113, e.g. a memory card. Here, the characteristic may also be output by way of the output unit 25. By way of example, the data may be output as text and/or as a speech signal and/or it may be represented graphically.

Figure 2:
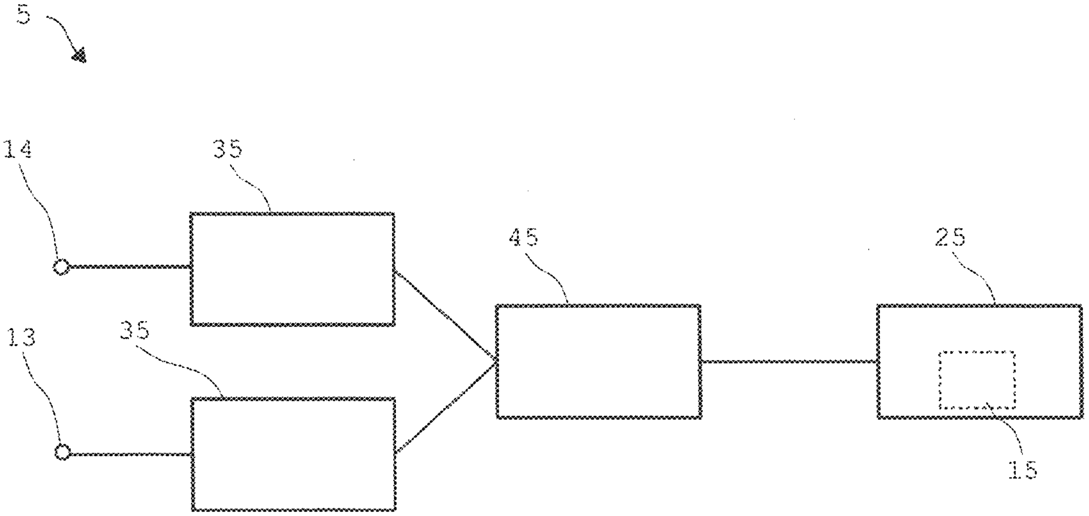
FIG. 2 shows a very schematic chart for sketching out the functionality of the ventilator.
Figure 3:
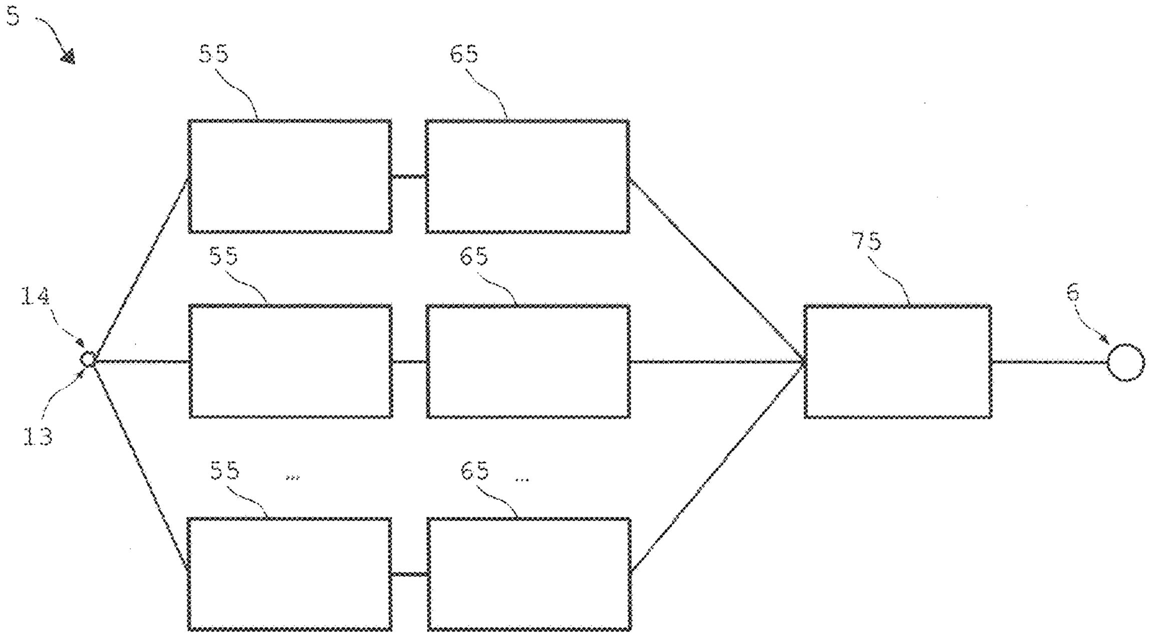
FIG. 3 shows a further very schematic chart for sketching out the functionality of the ventilator.

FIG. 2 and FIG. 3 show the structure of the monitoring device 5 in a very schematic illustration.

In FIG. 2, the monitoring device 5 comprises an evaluation unit 45 which processes at least one signal 14 connected to the set and/or current ventilation pressure 4. Here, the evaluation unit 45 processes at least one second signal 13 which is related to the respiratory phase 3 of the patient. In the configuration shown here, the respiratory air flow 23 of the patient is captured to this end. On the basis of the respiratory air flow 23, it is possible to particularly reliably capture the respiratory phase 3 and, for example, the curve of the inhalation phases and exhalation phases.

The output signal of the evaluation unit 45, in particular an identified lack of synchronicity, can be fed back to the control device of the ventilation device in order to modify the sensitivity of the inspiratory and/or expiratory trigger and/or the backup frequency and/or the inspiration duration.

By way of example, the ventilation pressure 4 or therapy pressure and the respiratory air flow 23 can be measured by pressure and flow sensors or ascertained from the operating states of a turbine. The signals captured thereby are then provided to the monitoring device 5 and processed by the latter.

Here, the monitoring device 5 comprises two pre-processing units 35 for the incoming signals 13, 14. By way of example, preprocessing can be carried out in the form of smoothing the signals 13, 14 or of removing a long-term average from the signals 13, 14.

The output unit 25 may be a screen or else a loudspeaker, by means of which there is a warning notification or a speech output. The output unit 25 may be situated directly in the ventilator 1 or it may be connected therewith, at least intermittently, by way of a data connection.

The data connection may contain, for example, a USB cable, a network cable, a mobile radio modem, and LPWA modem or a Bluetooth modem.

It is also possible for the results of the output unit 25 to be stored in a database, from where they can be obtained at a later time and represented by the output unit 25. The output unit 25 may also comprise an internal storage device 15.

Preferably, further characteristics or measures which are related to the ventilation success, e.g. leaks, volume, respiratory frequency, apnea-hypopnea index, are output together with the characteristic 6 for the synchronicity or the synchronicity measure.

The evaluation unit 45 is illustrated in more detail in FIG. 3. On the basis of the evaluation unit 45, the monitoring device 5 identifies at least two, and preferably all six, of the following types of lack of synchronicity here:

1. Missed inspiratory respiratory exertion of the patient; P pressure profile was not triggered.
2. Missed expiratory respiratory exertion of the patient; EPAP pressure profile was not triggered.
3. IPAP pressure profile was triggered belatedly and it does not assist the patient with inhalation at the ideal moment.
4. EPAP pressure profile was triggered belatedly and does not assist the patient with exhalation at the ideal moment.
5. IPAP pressure profile was triggered prematurely and it forces the patient to premature inhalation or to resist the inhalation (fighting).
6. EPAP pressure profile was triggered prematurely and it forces the patient to premature exhalation or to resist the exhalation (fighting).

Here, a detector unit 55 is provided in each case for identifying the types of lack of synchronicity. For the purposes of counting the frequency with which the types of lack of synchronicity occur, respectively one frequency ascertainment means 65 is provided for each type. A single detector unit 55 or single frequency ascertainment means 65 may also be able to ascertain and count, respectively, at least two of the six aforementioned types of lack of synchronicity.

The frequency of the individual types of lack of synchronicity is ascertained here for the evaluation time period and ascertained relative to the duration of the evaluation time period or the number of breaths or appliance triggers within the evaluation time period as characteristic 6 or as a measure of the synchronicity for each of the at least two detecting units 55.

As an alternative to counting individual respiratory phases 3 or breaths, the ascertainment of the frequency may also be ascertained by the duration and strength of the presence of a specific pattern.

In a further step, at least one overall characteristic 6 or one overall measure of the synchronicity is ascertained for the evaluation time period by an integration unit 75. The overall measure and, optionally, the individual measures of the synchronicity as well are transferred as described above to the output unit 25 and are presented there.

Here, the integration means 75 may add the individual frequencies of the lack of synchronicity or of the present synchronicity or, for example, if indications for a number of types of lack of synchronicity are present at the same time, adopt the maximum measure for the frequency or probability of an occurring type of lack of synchronicity.

Figure 5:
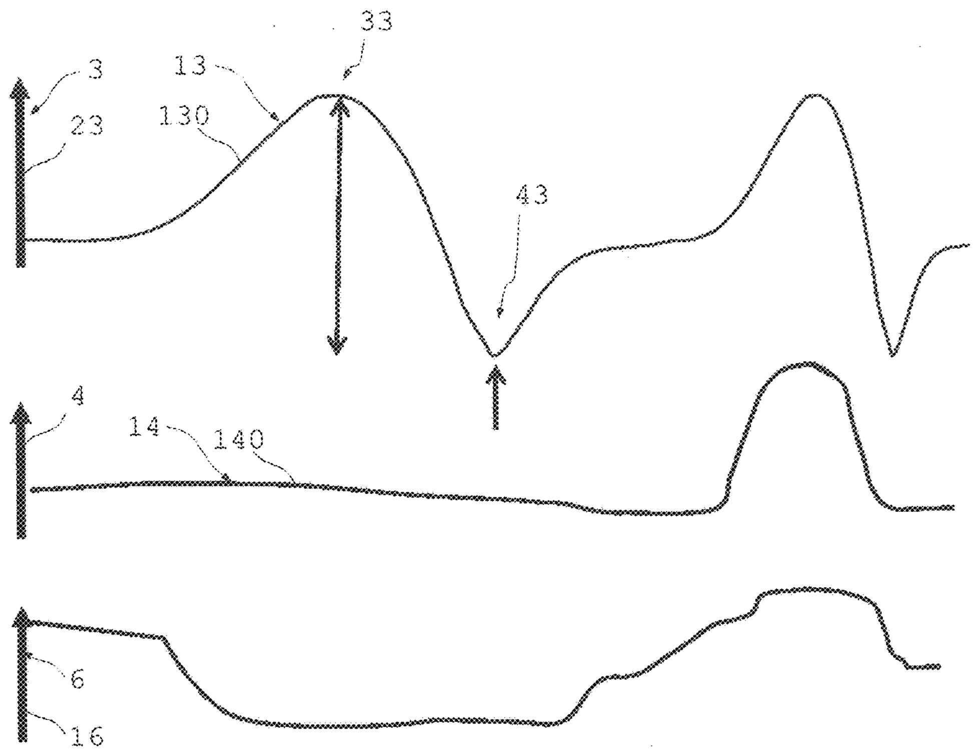
FIG. 5 shows a purely schematic diagram for sketching out a lack of synchronicity between respiratory phase and ventilation pressure.

Now, the functionality of the monitoring device 5 or of the corresponding detector unit 55 for monitoring and identifying missed inspiratory respiratory exertions is described with reference to FIG. 5. The middle diagram sketches out the curve 140 of the signal 14 of the ventilation pressure 4 over time. The upper diagram sketches out the corresponding curve 130 of the signal 13 of the respiratory air flow 23 over time. The lower diagram shows a similarity measure 16 between pressure signal 14 and (respiratory air) flow signal 13, which may serve, for example, as a characteristic 6 for the synchronicity.

After the preceding expiration has run its course, the appliance 1 or the ventilation device 2 is in a waiting time for the next inspiration. Should an inspiratory respiratory exertion 33 of the patient remain unidentified during this time, for example because it is too small or covered by disturbance signals or if it falls into a period of time with a greatly reduced trigger sensitivity, an unexpected second expiration 43 of the patient or at least an unexpected further respiratory air flow decrease will be detected.

As a consequence, a counter for missed breaths is incremented.

Missed expirations may be detected analogously thereto.

In particular, a missed breath is identified if, during the waiting phase for the inspiration, a respiratory air flow 23 of <−4 l/min is identified for a period of time of more than half a second and less than 6 seconds or if a drop in the respiratory air flow 23 of more than 5 l/min in relation to the highest respiratory air flow 23 obtained during the waiting phase is detected for more than half a second and less than 6 seconds. Such thresholds facilitate a reliable identification.

Alternatively, or in a complementary manner, it is possible to ascertain a similarity measure 16 between the pressure signal 14 and the respiratory air flow signal 13. By way of example, it may be embodied as a correlation index between the two signals 13, 14 with a suitable comparison index, for example the autocorrelation index of the flow signal 13. A high similarity means a good synchronicity between the pressure signal 14 and flow signal 13. A low similarity suggests flow or pressure changes, which are not responded to in the respective other signal 13, 14. If the similarity falls below a defined threshold, e.g. a correlation coefficient of less than 0.3, for more than one second, a counter for missed breaths is incremented.

Alternatively, missed breaths may also be ascertained by comparison between the pressure signal 14 and flow signal 13 with the aid of pattern recognition. Here, a deflection of one of the two signals 13, 14 which is not responded to as per expectation in the other signal 13, 14 is likewise sought after.

The pattern recognition may preferably contain a fuzzy logic. The probability that the patient is in a certain respiratory phase is ascertained by certain rules, for example by way of the value of the respiratory flow, its gradient and the temporal distance to certain respiratory phase transitions. Here, there preferably are at least the respiratory phases of inspiration and expiration; there particularly preferably is a finer subdivision into e.g. early inspiration, mid inspiration, etc. The probability for the presence of a certain respiratory phase is subsequently compared to the curve of the pressure signal, or it is alternatively used directly for the pressure control of the ventilation system.

Additionally, or alternatively, use can be made of a prediction method for a signal that is related to the respiratory flow, e.g. a Kalman filter, to predict the curve of the respiratory phase and control the triggering and pressure profiles thereby in such a way that a reduced delay time arises between the respiratory flow signal 23 and pressure signal 14. Prediction methods are characterized in that a value of the measurement variable is already predicted on the basis of at least one earlier measurement value and/or an earlier increase of the measurement variable and at least one saved model equation before the current measurement value is measured. Hence, the pressure control at the current time is already influenced by the predicted value, i.e. accelerated by at least one sampling time. A lack of synchronicity may likewise be ascertained by way of the deviation between at least one currently measured measurement variable and at least one value predicted therefor. Preferably, the deviation can additionally be used to determine the weighting with which at least one measurement value and at least one predicted value of at least one measurement variable are included in the pressure control and/or in the triggering.

Alternatively, missed breaths may also be identified by way of jumps in parameters which are derived from respiratory flow 13 or pressure profile, e.g. respiratory frequency or volume. In the normal case, these parameters only vary by a few % per breath. However, if a breath is missed, the frequency suddenly halves or drops to the saved backup frequency. Consequently, it is possible to predetermine an absolute or relative threshold for the respiratory frequency, e.g. 70% of the spontaneous respiratory frequency. A missed breath is detected if the current respiratory frequency drops below this threshold.

The frequency ascertainment means counts the number of missed breaths and the number of identified breaths within a time interval, preferably 1 min, 2 min, 5 min, 10 min, 15 min, 20 min or 30 min. The synchronicity measure 6 is ascertained from the ratio of the two breath counts. In the case of a percentage ascertainment, 100 means that all breaths were recognized and 0 means that all breaths were missed. A measure 6 for lack of a synchronicity would have an inverse scale, i.e. 100 for missing all breaths and 0 for identifying all breaths.

Figure 6:
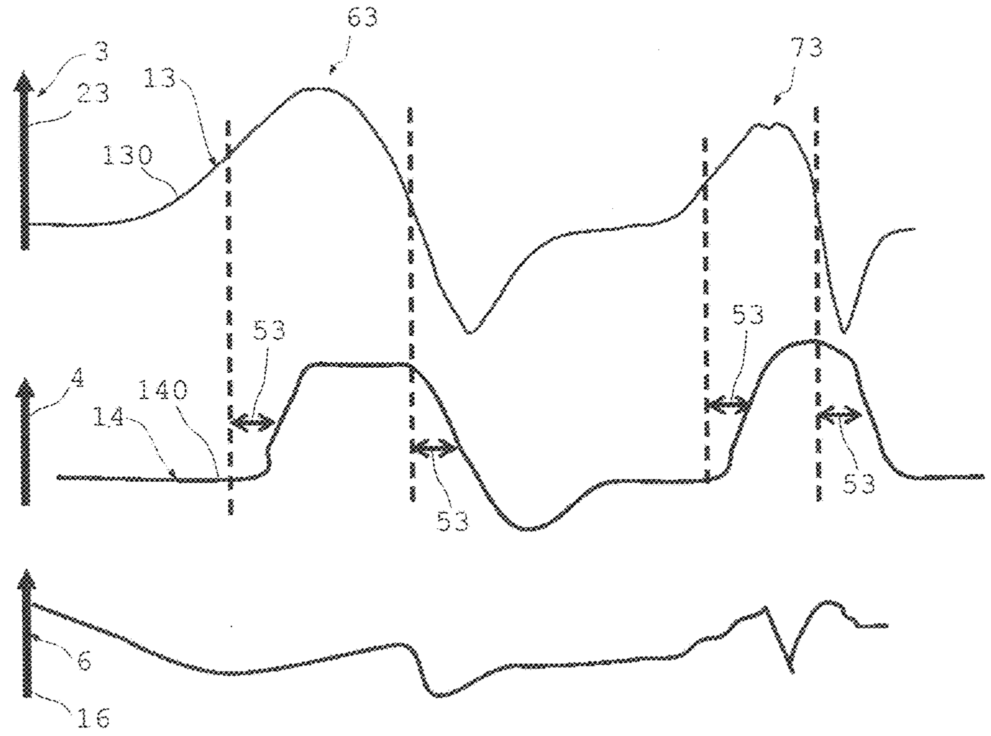
FIG. 6 shows a further diagram for sketching out a lack of synchronicity between respiratory phase and ventilation pressure.

Now, monitoring and recognizing target ventilation pressures 4 set belatedly in relation to the respiratory phase 3 of the patient is described with reference to FIG. 6. The curve 140 of the signal 14 of the ventilation pressure 4 over time is sketched out in the middle diagram. The upper diagram sketches out the corresponding curve 130 of the signal 13 of the respiratory air flow 23 over time. The lower diagram shows the similarity measure 16 between the pressure signal 14 and respiratory air flow signal 13.

There is a temporal delay 53 between target pressure and respiratory phase 3 in the case of a belated appliance reaction. The time delay 53 of the ventilation pressure 4 or pressure profile 24 in relation to the flow curve 130 can be determined on the basis of the temporal localization of certain characteristic functional features. Examples include the temporal distance between the minima or maxima of the two signals 13, 14 or between the points with maximum gradient.

In the normal case, the pressure profile 24 should follow the respiratory flow with a time lag of between 0 and 100 ms. If the delay is significantly more than 100 ms, the assumption of a restricted synchronicity or of a lack of synchronicity can be made.

A long delay 53 when identifying breaths may lead to the time between two breaths exceeding the maximum waiting time and the appliance triggering a mandatory breath 73. Reference sign 63 shows a spontaneous breath in the signal curve 130.

Alternatively, or in a complementary manner, the delay may be ascertained by way of a similarity measure 16 between the pressure signal 14 and flow signal 13, for example carried out as a correlation index between the two signals with a suitable comparison index, for example the correlation index between the flow signal 13 and the pressure signal 14 displaced forward in time. If the pressure signal 14 is repeatedly displaced and correlated, it is possible to find the delay time 53 as the temporal displacement with the highest correlation index between pressure signal 14 and flow signal 13. In this way, it is likewise possible to determine whether the delay 53 is significantly longer than 100 ms.

Alternatively, delayed pressure profiles 24 or target pressures may also be ascertained by a comparison between the pressure signal 14 and flow signal 13 with the aid of pattern recognition. Here, the time duration 53 which leads to the highest similarity of the signals 13, 14 when one of the two signals 13, 14 is displaced is likewise sought after.

Here, the frequency ascertainment means 65 counts the number of breaths with a critical delay 53 and the number of breaths identified in a time interval, preferably 1 min, 2 min, 5 min, 10 min, 15 min, 20 min or 30 min. The synchronicity measure 6 is ascertained from the ratio of the two breath counts. In the case of a percentage ascertainment, 100 means that all breaths were identified and 0 means that all breaths were missed. A measure 6 for a lack of synchronicity would have an inverse scaling, i.e. 100 for all breaths missed and 0 for all breaths identified. Alternatively, the frequency ascertainment means 65 measures the mean delay of the pressure signal 14 in relation to the flow signal 13. If this is more than 100 ms, the synchronicity measure 6 drops or the measure 6 for the lack of synchronicity increases.

Figure 7:
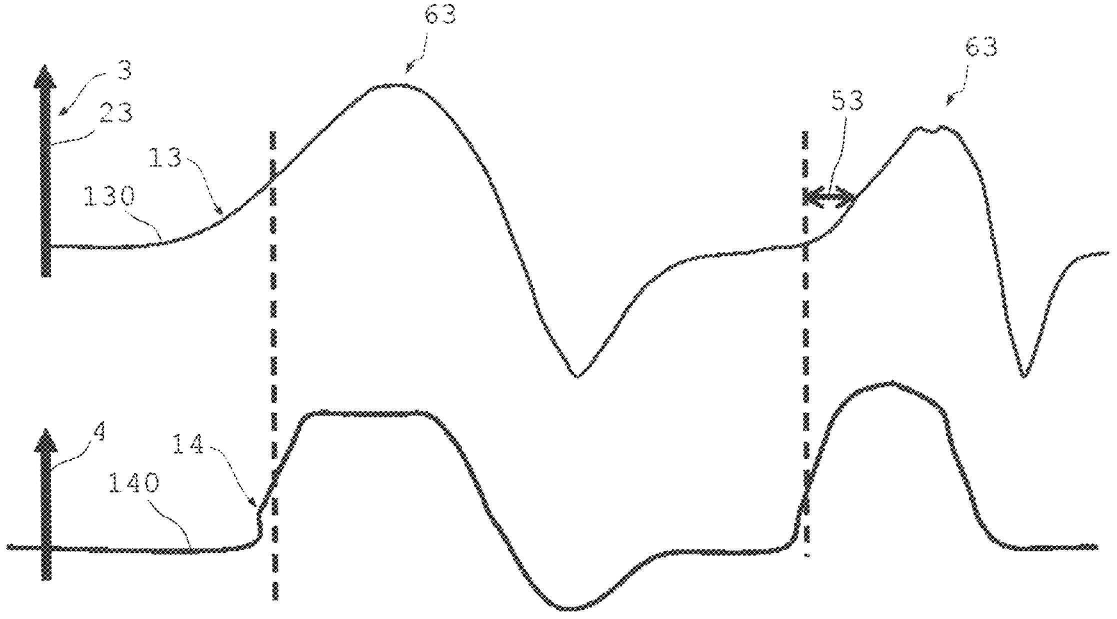
FIG. 7 shows another diagram for sketching out a lack of synchronicity between respiratory phase and ventilation pressure.

Now, monitoring and identifying target ventilation pressures 4 which were set prematurely in relation to the respiratory phase 3 of the patient is described with reference to FIG. 7. The lower diagram sketches the curve 140 of the signal 14 of the ventilation pressure 4 over time. The upper diagram sketches out the corresponding curve 130 of the signal 13 of the respiratory air flow 23 over time.

A premature appliance reaction or a leading pressure profile 24 arises, for example, by the ventilator 1 triggering on its own accord. The delay time 53 of the flow curve 130 in relation to the pressure curve 140 or the pressure profile 24 can be determined on the basis of a temporal localization of certain characteristic functional features. By way of example, the temporal distance between the minima or maxima of the two signals 13, 14 or between the points with maximum gradient is used to this end.

In the case of spontaneous breaths 63, there is always a slight delay of the pressure signal 14 in relation to the flow signal 13 in the case of a good synchronicity as the appliance 1 reacts to the respiration of the patient. In the ideal case, the delay is less than 100 ms. However, if there is no delay of the pressure signal 14 in relation to the flow signal 13, as in the case of a mandatory breath 73, the assumption can be made that the appliance 1 has triggered the breath on account of triggering on its own accord and has consequently induced the patient flow.

There even is a delay of the flow signal 13 in relation to the pressure signal 14 if the patient perceives the premature triggering by the appliance 1 as uncomfortable and attempts to refuse ventilation (fighting). Alternatively, the flow signal 13 may be greatly reduced as a result of the fighting.

By way of example, a prematurely triggered breath is identified if the delay 53 of the pressure signal 14 in relation to the flow signal 13 is less than 10 ms, wherein negative values may also occur and likewise indicate a prematurely triggered breath.

The identification of prematurely triggered expirations is effectuated in an analogous manner. Alternatively, or in a complementary manner, prematurely triggered breaths may also be identified by way of jumps in parameters which are derived from the respiratory flow curve 130 or pressure curve 140, e.g. respiratory frequency or volume. In the normal case, these parameters only vary by a few % per breath. However, if breaths are triggered prematurely, the frequency suddenly increases. Consequently, it is possible to predetermine an absolute or relative threshold of the respiratory frequency, e.g. 130% of the spontaneous respiratory frequency. If the current respiratory frequency increases above this threshold a prematurely triggered breath is detected.

Here, the frequency ascertainment means 65 counts the number of prematurely triggered breaths and the number of identified breaths in a time interval, preferably 1 min, 2 min, 5 min, 10 min, 15 min, 20 min or 30 min. The synchronicity measure 6 is ascertained from the ratio of the two breath counts. In the case of a percentage ascertainment, 100 means that all breaths were triggered correctly and 0 means that all breaths were triggered prematurely. A measurement 6 for a lack of synchronicity would have an inverse scaling, i.e. 100 for all breaths triggered prematurely and 0 for all breaths triggered correctly.

LIST OF REFERENCE SIGNS

| | |
|---|---|
| 1 | Ventilator |
| 2 | Ventilation device |
| 3 | Respiratory phase |
| 4 | Ventilation pressure |
| 5 | Monitoring device |
| 6 | Characteristic |
| 12 | Control device |
| 13 | Signal (respiratory phase) |
| 14 | Signal (ventilation pressure) |
| 15 | Storage device |
| 16 | Similarity measure |
| 22 | Sensor device |
| 23 | Respiratory air flow |
| 24 | Pressure profile |
| 25 | Output unit |
| 33 | Inspiration (missed) |
| 35 | Pre-processing unit |
| 43 | Expiration (unexpected) |
| 45 | Evaluation unit |
| 53 | Delay |
| 55 | Detector unit |
| 63 | Breath (spontaneous) |
| 65 | Frequency ascertainment means |
| 73 | Breath (mandatory) |
| 75 | Integration unit |
| 101 | Blower device |
| 102 | Respiration interface |
| 103 | Operating elements |
| 105 | Ventilation mask |
| 106 | Head gear |
| 107 | Coupling element |
| 108 | Exhalation element |
| 109 | Connection tube |
| 110 | Pressure measuring tube |
| 111 | Input nozzle |
| 112 | Coupling device |
| 113 | Storage medium |
| 114 | User interface |
| 130 | Curve (respiratory phase) |
| 140 | Curve (ventilation pressure) |

What is claimed is:

1. A ventilator, wherein the ventilator comprises at least one ventilation device which is suitable and configured for producing at least one respiratory gas flow for ventilating a patient and setting the respiratory gas flow to at least one ventilation pressure depending on at least one respiratory phase of the patient, and further comprises at least one monitoring device which is suitable and configured for monitoring a synchronicity between respiratory phase and ventilation pressure by capturing at least one characteristic signal for the ventilation pressure and at least one characteristic signal for the respiratory phase of the patient and comparing the at least one characteristic signal for the ventilation pressure and the at least one characteristic signal for the respiratory phase to one another and determining at least one characteristic for the synchronicity based on the comparison, the monitoring device being further suitable and configured for identifying at least one type of lack of synchronicity and using said at least one type of lack of synchronicity for determining the characteristic of the synchronicity, the at least one type of lack of synchronicity being taken from (i) target ventilation pressures specified prematurely in relation to the respiratory phase of the patient; (ii) target ventilation pressures specified belatedly in relation to the respiratory phase of the patient; (iii) target ventilation pressures missed in relation to the respiratory phase of the patient, the target ventilation pressures missed in relation to the respiratory phase of the patient comprising at least one missed target expiration pressure and/or the target ventilation pressures specified prematurely in relation to the respiratory phase of the patient comprising a premature target inspiration pressure and/or a premature target expiration pressure and/or the target ventilation pressures specified belatedly in relation to the respiratory phase of the patient comprising a belated target inspiration pressure and/or a belated target expiration pressure; and wherein the monitoring device is suitable and configured for identifying a characteristic signal representing the exhalation phase by virtue of a respiratory air flow of the patient dropping below at least one threshold, the at least one threshold defining a respiratory air flow of less than or equal to 4 l/min for a period of time of more than half a second and less than six seconds and/or a drop in the respiratory air flow of at least 5 l/min in relation to a maximum value of the respiratory air flow for a period of time of more than half a second and less than six seconds.

2. The ventilator of claim 1, wherein the target ventilation pressures missed in relation to the respiratory phase of the patient comprise at least one missed target expiration pressure.

3. The ventilator of claim 1, wherein the target ventilation pressures specified prematurely in relation to the respiratory phase of the patient comprise a premature target inspiration pressure and/or a premature target expiration pressure.

4. The ventilator of claim 1, wherein the target ventilation pressures specified belatedly in relation to the respiratory phase of the patient comprise a belated target inspiration pressure and/or a belated target expiration pressure.

5. The ventilator of claim 1, wherein the monitoring device is suitable and configured for identifying a missed target inspiration pressure by virtue of the at least one characteristic signal for the respiratory phase at a defined time representing an exhalation phase and by virtue of the at least one characteristic signal for the ventilation pressure indicating that the last ventilation pressure set before the defined time is a target expiration pressure and not a target inspiration pressure.

6. The ventilator of claim 5, wherein the monitoring device is suitable and configured for identifying a characteristic signal representing the exhalation phase by virtue of a respiratory air flow of the patient dropping below at least one threshold, the at least one threshold defining a drop in the respiratory air flow of at least 5 l/min in relation to a maximum value of the respiratory air flow for a period of time of more than half a second and less than six seconds.

7. The ventilator of claim 1, wherein the monitoring device is suitable and configured for identifying a belated target ventilation pressure by virtue of at least one characteristic functional feature in a time curve of the at least one characteristic signal for the ventilation pressure occurring with a delay in relation to a corresponding characteristic functional feature in a time curve of the at least one characteristic signal for the respiratory phase and by virtue of the delay reaching at least one threshold, which threshold is at least 100 ms.

8. The ventilator of claim 7, wherein the threshold is at least 150 ms.

9. The ventilator of claim 1, wherein the monitoring device is suitable and configured for identifying a premature target ventilation pressure by virtue of at least one characteristic functional feature in a time curve of the at least one characteristic signal for the ventilation pressure occurring with a delay in relation to a corresponding characteristic functional feature in a time curve of the at least one characteristic signal for the respiratory phase and by virtue of the delay dropping below at least one threshold, which threshold is not more than 10 ms.

10. The ventilator of claim 9, wherein the threshold is not more than 5 ms.

11. The ventilator of claim 1, wherein the monitoring device is suitable and configured for identifying a missed and/or premature target ventilation pressure by virtue of at least one ventilation parameter derived from the at least one characteristic signal for the ventilation pressure and/or the at least one characteristic signal for the respiratory phase reaching or dropping below at least one threshold.

12. The ventilator of claim 1, wherein the monitoring device is suitable and configured for identifying an occurrence of at least one type of lack of synchronicity by virtue of at least one similarity measure between the at least one characteristic signal for the respiratory phase and the at least one characteristic signal for the ventilation pressure reaching or dropping below at least one threshold.

13. The ventilator of claim 1, wherein the monitoring device is suitable and configured for ascertaining a missed target ventilation pressure by virtue of at least one pattern recognition by searching for at least one characteristic curve in the at least one characteristic signal for the respiratory phase or in the at least one characteristic signal for the ventilation pressure which does not occur in the other characteristic signal.

14. The ventilator of claim 1, wherein the monitoring device is suitable and configured for ascertaining a belated and/or premature target ventilation pressure by way of pattern recognition by searching for at least one time duration in time curves in the at least one characteristic signal for the respiratory phase and in the at least one characteristic signal for the ventilation pressure which leads to a greatest similarity of these characteristic signals in the case of a temporal displacement of at least one of these characteristic signals.

15. The ventilator of claim 1, wherein the monitoring device is suitable and configured for counting a frequency of an occurrence of at least one of the types of lack of synchronicity (i) to (iii) during a defined time interval and taking the frequency of the occurrence into account in the characteristic.

16. A ventilator, wherein the ventilator comprises at least one ventilation device which is suitable and configured for producing at least one respiratory gas flow for ventilating a patient and setting the respiratory gas flow to at least one ventilation pressure depending on at least one respiratory phase of the patient, and further comprises at least one monitoring device which is suitable and configured for monitoring a synchronicity between respiratory phase and ventilation pressure by capturing at least one characteristic signal for the ventilation pressure and at least one characteristic signal for the respiratory phase of the patient and comparing the at least one characteristic signal for the ventilation pressure and the at least one characteristic signal for the respiratory phase to one another and determining at least one characteristic for the synchronicity based on the comparison, the monitoring device further influencing a function of a control device comprised in the ventilator by way of information feedback about an occurrence of a lack of synchronicity, or type, frequency and strength thereof and being suitable and configured for identifying a characteristic signal representing the exhalation phase by virtue of a respiratory air flow of the patient dropping below at least one threshold, the at least one threshold defining a respiratory air flow of less than or equal to 4 l/min for a period of time of more than half a second and less than six seconds and/or a drop in the respiratory air flow of at least 5 l/min in relation to a maximum value of the respiratory air flow for a period of time of more than half a second and less than six seconds.

17. The ventilator of claim 16, wherein the information feedback influences the control device to change trigger sensitivities for spontaneous inspirations and expirations.

18. The ventilator of claim 16, wherein the information feedback influences the control device to change a backup frequency.

19. The ventilator of claim 16, wherein the information feedback influences the control device to change an inspiration duration for mandatory inspirations and expirations.

20. The ventilator of claim 16, wherein the information feedback influences the control device to change an inspiratory positive airway pressure (IPAP).

* * * * *